United States Patent
Buchanan

(10) Patent No.: US 10,420,629 B2
(45) Date of Patent: Sep. 24, 2019

(54) ENDODONTIC INSTRUMENTS WITH PILOT TIPS AND PARABOLIC CUTTING FLUTES

(71) Applicant: ORMCO CORPORATION, Orange, CA (US)

(72) Inventor: L. Stephen Buchanan, Santa Barbara, CA (US)

(73) Assignee: ORMCO CORPORATION, Orange, CA (US)

( * ) Notice: Subject to any disclaimer, the term of this patent is extended or adjusted under 35 U.S.C. 154(b) by 59 days.

(21) Appl. No.: 14/048,448

(22) Filed: Oct. 8, 2013

(65) Prior Publication Data

US 2014/0057226 A1 Feb. 27, 2014
US 2018/0360561 A9 Dec. 20, 2018

Related U.S. Application Data

(60) Division of application No. 11/104,979, filed on Apr. 12, 2005, now abandoned, which is a continuation of application No. PCT/US03/33360, filed on Oct. 20, 2003.

(60) Provisional application No. 60/419,662, filed on Oct. 18, 2002.

(51) Int. Cl.
*A61C 5/40* (2017.01)
*A61C 5/42* (2017.01)

(52) U.S. Cl.
CPC . *A61C 5/40* (2017.02); *A61C 5/42* (2017.02)

(58) Field of Classification Search
CPC .. A61C 5/023; A61C 5/02; A61C 5/40; A61C 5/42
USPC .................................................. 433/102, 224
See application file for complete search history.

(56) References Cited

U.S. PATENT DOCUMENTS

| 4,260,379 A | * | 4/1981 | Groves | A61C 5/42 408/210 |
| 4,299,571 A | | 11/1981 | McSpadden | |
| 4,332,561 A | | 6/1982 | McSpadden | |
| 4,353,698 A | * | 10/1982 | McSpadden | A61C 5/50 433/122 |
| 4,536,159 A | | 8/1985 | Roane | |
| 4,611,508 A | | 9/1986 | Roane | |

(Continued)

FOREIGN PATENT DOCUMENTS

| EP | 0330173 A1 * | 8/1989 | A61C 5/023 |
| EP | 330173 A1 | 8/1989 | |

(Continued)

OTHER PUBLICATIONS

English Translation of LEVY (EP 0330173), obtained from www.espacenet.com on May 22, 2019 (Year: 2019).*

(Continued)

*Primary Examiner* — Cris L. Rodriguez
*Assistant Examiner* — Hao D Mai
(74) *Attorney, Agent, or Firm* — Michael Best & Friedrich LLP

(57) ABSTRACT

A series of multi-tapered parabolic implements is disclosed for endodontic use. The instruments comprise different sections: a pilot tip, a first portion adjacent the pilot tip and a second portion adjacent the shank. The two portions have different tapers. The tapers of the two different portions blend into each other along a parabola-shaped surface. The pilot tip is radiussed for ease of entry into a root canal with increased safety.

15 Claims, 9 Drawing Sheets

(56) References Cited

U.S. PATENT DOCUMENTS

| | | | |
|---|---|---|---|
| 4,836,780 A | 6/1989 | Buchanan | |
| 4,850,867 A | 7/1989 | Senia | |
| 5,026,284 A | 6/1991 | Martin | |
| 5,219,284 A | 6/1993 | Velvart et al. | |
| 5,658,145 A | 8/1997 | Maillefer et al. | |
| 5,746,597 A | 5/1998 | Maillefer et al. | |
| 5,752,825 A | 5/1998 | Buchanan | |
| 5,816,807 A * | 10/1998 | Matsutani | A61C 3/02 433/165 |
| 5,836,764 A | 11/1998 | Buchanan | |
| 5,842,861 A | 12/1998 | Buchanan | |
| 5,855,479 A | 1/1999 | Wong et al. | |
| 5,876,202 A * | 3/1999 | Berlin | A61C 3/02 408/230 |
| 5,897,316 A | 4/1999 | Buchanan | |
| 5,921,775 A | 7/1999 | Buchanan | |
| 5,947,730 A | 9/1999 | Kaldestad | |
| 6,042,375 A | 3/2000 | Riitano | |
| 6,074,209 A * | 6/2000 | Johnson | A61C 5/42 433/102 |
| 6,217,335 B1 | 4/2001 | Riitano et al. | |
| 6,409,506 B1 | 6/2002 | Graybill | |
| 6,702,579 B1 * | 3/2004 | Hoppe | A61C 5/42 433/102 |
| 2002/0028422 A1 * | 3/2002 | Kumar | A61C 8/0089 433/165 |
| 2003/0013067 A1 * | 1/2003 | Bleiweiss | A61C 5/023 433/102 |
| 2004/0121283 A1 * | 6/2004 | Mason | B23B 51/0081 433/102 |
| 2005/0106532 A1 * | 5/2005 | Deutsch | A61C 3/02 433/102 |

FOREIGN PATENT DOCUMENTS

| | | |
|---|---|---|
| WO | WO-0028915 A1 | 5/2000 |
| WO | WO-0219938 A1 | 3/2002 |

OTHER PUBLICATIONS

Weine, "The Effect of Preparation Procedures on Original Canal Shape and on Apical Foramen Shape", *Journal of Endodontics*, vol. 1, No. 8, Aug. 1975, pp. 255-262.

International Preliminary Examination Report in the corresponding International Application No. PCT/US03/33360 dated Dec. 27, 2004.

English language machine translation of EP0330173 A1, Aug. 1989.
English language translation of WO00/28915, May 2000.

* cited by examiner

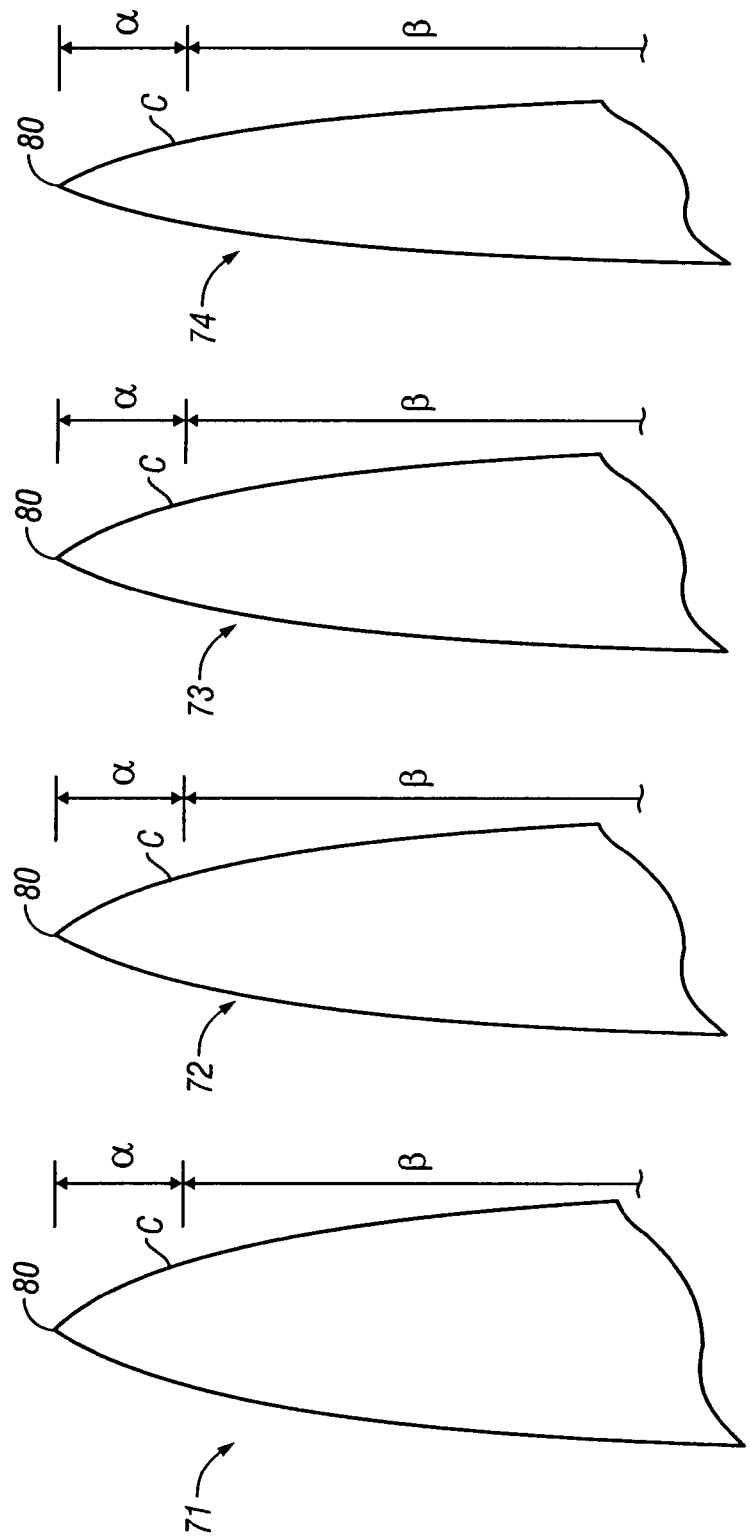

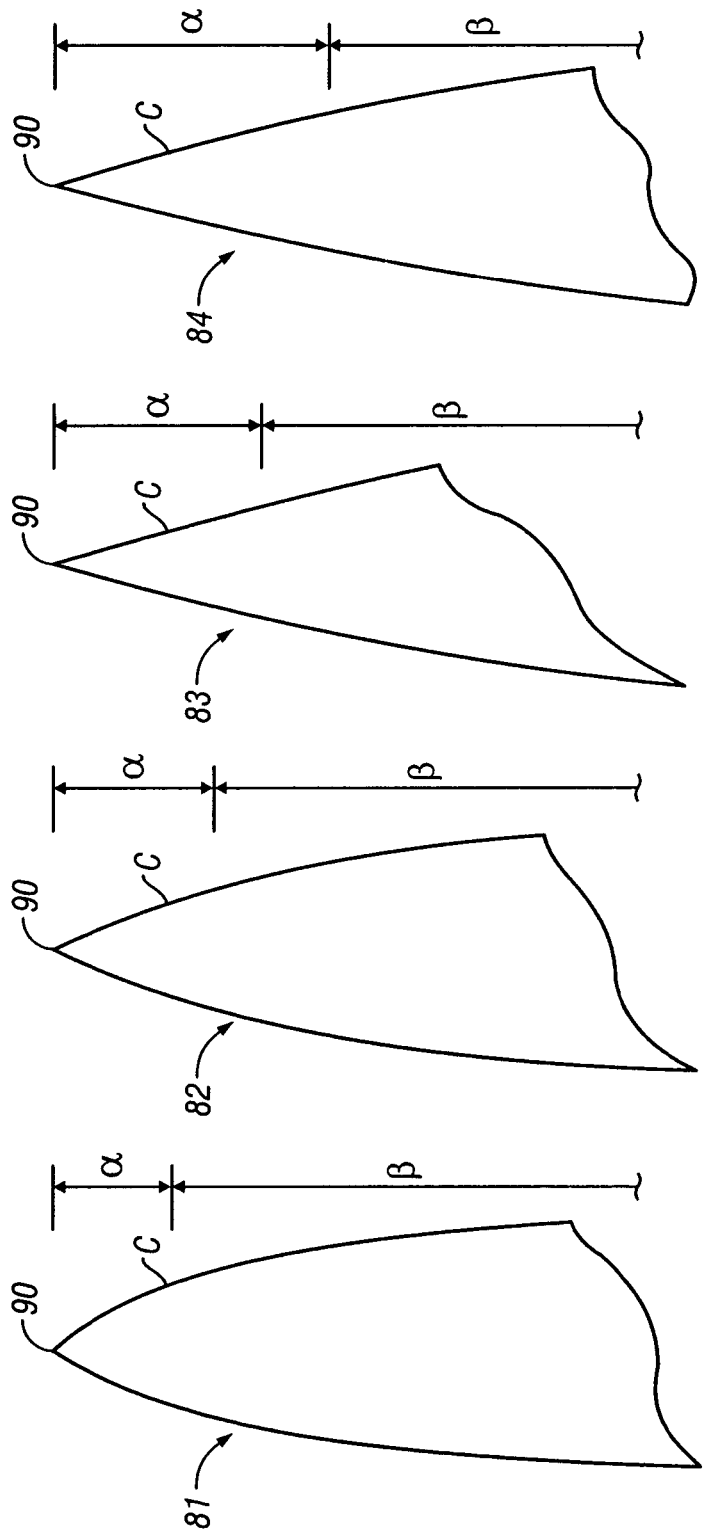

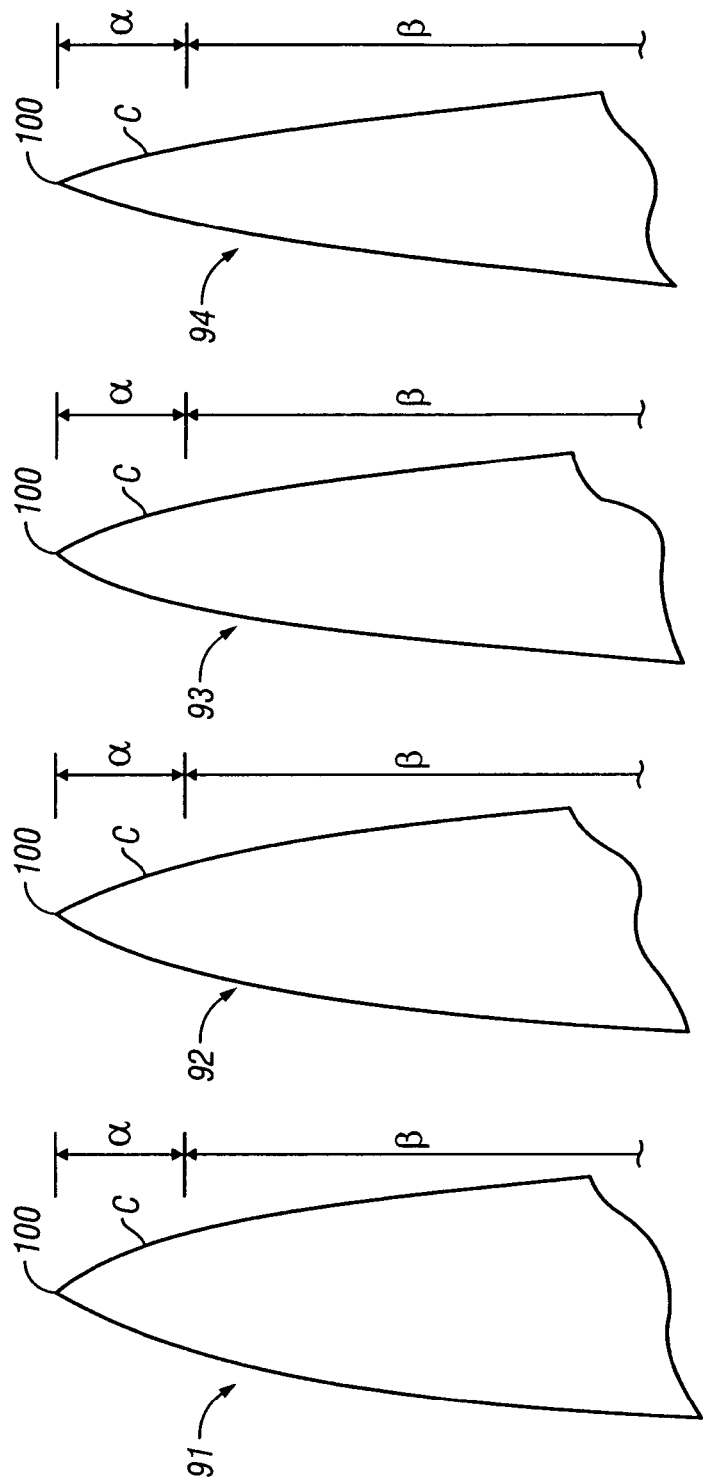

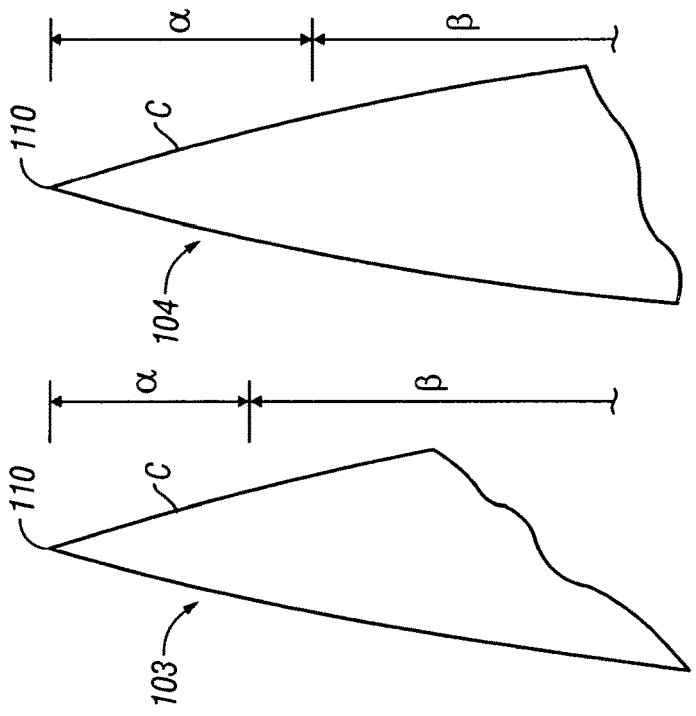
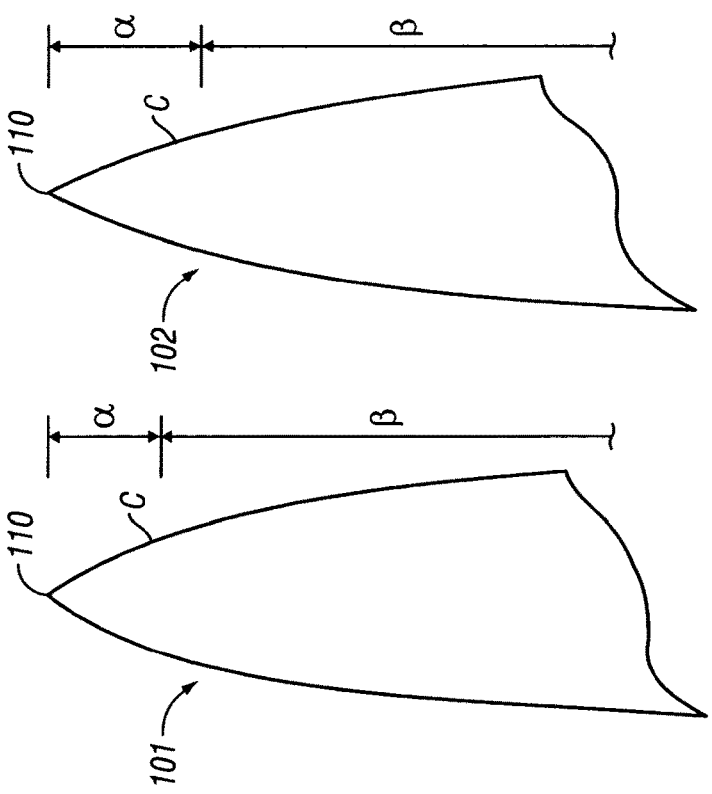

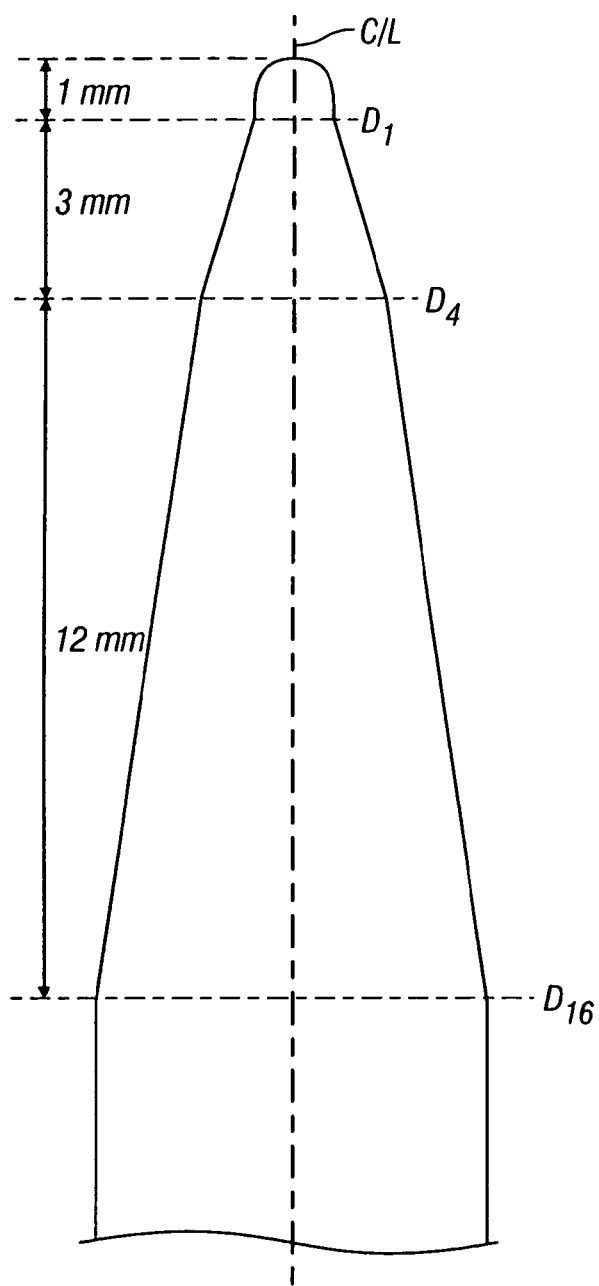
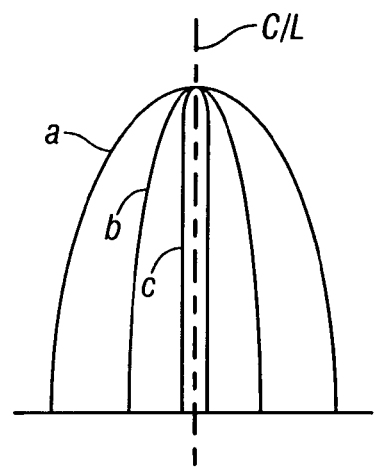
FIG. 12
FIG. 11

ENDODONTIC INSTRUMENTS WITH PILOT TIPS AND PARABOLIC CUTTING FLUTES

CROSS-REFERENCE TO RELATED APPLICATION

This application Divisional of U.S. patent application Ser. No. 11/104,979, filed Apr. 12, 2005, which is a continuation of PCT Application No. PCT/US03/33360, filed Oct. 20, 2003, which claims priority from U.S. Provisional Application No. 60/419,662, filed Oct. 18, 2002.

BACKGROUND OF THE INVENTION

Field of the Invention

The present invention relates generally to endodontic instruments and, more particularly, to cutting burs which are used in the creation of ideal access preparations into root canal systems of human teeth and to shaping files which are used to enlarge and shape the root canals present therein so that they may be prepared for filling.

Description of the Related Art

A relatively common but difficult dental procedure is the entry into and the cleaning, shaping, and filling of root canals in human teeth that have become pathologic. In the performance of a root canal procedure, a hole is first cut in the crown or exposed portion of the tooth, typically either in the biting surface of the tooth, for posterior teeth, or in the side of the tooth on the interior of the jaw for incisor teeth.

The creation of ideal access form has been difficult with available cutting tools, specifically preparing an ideal entry path for handpiece-driven files to effortlessly enter root canals. Cutting the correct entry path is critical because without a relatively straight approach for these rotary files, they are prone to breakage due to cyclic fatigue. Another difficult aspect of endodontic therapy has been the creation of a smooth transition between each of the access line-angles and the canal orifices apical to them. Leaving an irregularity at this transition level makes every introduction of a file, paper point, or gutta percha point into the root canal a challenge. When the line angle of the access preparation drops smoothly into the canal the rest of the procedure is easier and more controlled.

Several solutions have been offered by manufacturers, such as Peezo burs which come in different configurations and access burs with no cutting flutes or diamond grit on the tip of the instrument.

Peezo burs come in different configurations, two with different degrees of parabolic flute silhouettes, and another with a pilot tip, a quarter-round flute-tip radius with parallel shank flutes. All of these burs have cutting flute lengths of around 6-8 mm. The advantages of these burs when used in access procedures are the funnel shapes they make into canals, and the pilot tip which prevents ledge formation. Unfortunately, the flute length of these burs is only half the height of most access preparations, several of the Peezo designs are able to ledge canals, and those that have pilot tips are limited in their use because these passive guides are not of the ideal dimension.

Access burs with pilot tips but without flutes or diamond grit at their ends are an improvement over those burs that can cut ledges in access and canal walls. These burs are quite limited in their use as they only cut sideways. What is needed is an access bur that has flutes the full length of the access cavity, that cuts aggressively in apical and lateral directions, that will not ledge, and will always follow the canal path. After the access preparation is completed and each of the root canals present in the tooth is located and negotiated, small endodontic instruments known generally as root canal files are then used to clean out the material present in the root canal, and to impart a specific shape to the root canal so that filling material may be inserted into the root canal to seal it. However, many problems can occur during this process.

Most common is the uncontrolled transportation of the original canal path. This occurs with traditional root canal files having aggressive tip geometry, as described by Roane U.S. Pat. No. 4,536,159, as well as with other file designs such as those by McSpadden in U.S. Pat. Nos. 4,299,571 and 4,332,561, and in Maillefer et al. U.S. Pat. No. 5,658,145. Files with passive radiussed tip geometries, such as those described by Buchanan in previous patents, such as U.S. Pat. Nos. 4,836,780, 5,752,825, 5,836,764, 5,842,861, 5,897,316, and 5,921,775 faithfully follow the original canal path as they cut, but these safe file tips give up a certain amount of cutting efficiency to more aggressive designs. While clinicians initially react positively to the added cutting efficiency of these files, they find in a short time that apical lacerations can easily occur if length has been mis-determined or if the files are held at length for more than one second (Manufacturer's cautions in DFU).

Furthermore, there has been some concern that the relatively narrow apical shapes created by the files described by Buchanan might not clean the ends of root canals as well as a technique which enlarged the end of root canals more. The apical stop preparation apparently accomplished this but, as Weine showed—"The Effect of Preparation Procedures on Original Canal Shape and on Apical Foramen Shape", Journal of Endodontics, vol. 1, No. 8, August 1975, pp. 225-262—it is difficult to create these larger apical shapes in root canals without damaging the root.

McSpadden, as disclosed in his U.S. Pat. No. 4,299,571, designed a pilot tip for root canal files which attempted to resolve this problem. Unfortunately, the pilot tips of this design were 3 mm long and the cutting flutes behind them had a small 0.02 mm/mm taper. The function of this file concept was limited because the pilot tip often bound in the canal before the flutes contacted the canal wall, so larger shapes were impossible with these files.

SUMMARY OF THE INVENTION

The objective of the present invention is to allow faster and safer cutting tools to enter and shape root canals. This is realized primarily through a design logic incorporating sophisticated pilot tip geometry, parabolic cutting flutes in the region behind the pilot tip (referred to herein as the "alpha" or α region), and flutes of a consistent length and lesser taper comprising the region (referred to herein as the "beta" or β region) between the alpha region and the shank. This design concept is applied to access preparation burs, to initial enlargement files, and to finishing files.

Files disclosed in my prior application, Ser. No. 10/630,028, are provided with two distinct degrees of taper for the two portions of each file. I contemplate as part of the present invention additional groups of multi-taper files where the taper at the tip is one value, the taper of the flute portion adjacent the shank is another value, and there is a gradual but continuous change from one value to the other with distance from the tip. In other words, files of these groups, are not limited to two fixed tapers for corresponding sections of the flute but rather the change of taper from tip to shank portion occurs over a radius. I refer to these types of files in which the change of taper occurs over a radiussed section as parabolic files. These are incorporated in my parabolic system of endodontic implements.

Files of the type described herein are improved significantly if they are provided with a radiussed pilot tip. Parabolic shaping files with radiussed pilot tips are far safer by virtue of the radiussed tip and are virtually guaranteed to eliminate the danger of ledging in a root canal.

In one preferred arrangement of my invention, the radiussed pilot tips of different parabolic shaping files in a set are 1 mm in length and have eight different diameters, taken at the 1 mm point, for eight different parabolic shaping files. The alpha taper section behind the non-cutting pilot tip is 3 mm in length and has a 0.10 mm/mm slope for all files of this parabolic file system. The beta taper which extends to the shank is 12 mm in length and has a 0.05 mm/mm angle or slope for all files. With a 1 mm pilot tip length, an alpha length of 3 mm, and a shank length of 12 mm, all instruments have the traditional 16 mm limit to the shank-end fluted portion. These are provided in hand and handpiece-driven versions, with the hand files made in both left-hand and right-hand flute directions.

Various critical dimensions for these parabolic shaping files are set out in the following Table I. The dimensions are given in millimeters.

TABLE I (In millimeters)

| D1 | D4 | D16 |
|----|----|-----|
| .1 | .4 | 1.05 |
| .2 | .5 | 1.15 |
| .3 | .6 | 1.25 |
| .4 | .7 | 1.35 |
| .6 | .9 | 1.55 |
| .8 | 1.1 | 1.75 |
| 1.0 | 1.3 | 1.95 |
| 1.3 | 1.6 | 2.25 |

D1 is the diameter at 1 mm from the end of the file. D4 is the diameter at 4 mm from the end (3 mm from the tip). D16 is the diameter at 16 mm from the end (15 mm from the tip).

For negotiating instruments, the parabolic negotiating files are simpler and fewer in number than the parabolic shaping files described above. These are provided in tip diameters of 0.06 mm, 0.08 mm, 0.10 mm, and 0.15 mm and all have 16 mm of 0.02 mm/mm tapered flute length. A second series incorporates variable tapers between files and some different tip diameters; specifically a 075-0.02, a 10-0.03, a 15-0.04, and a 20-0.05. Both series have the unique radiussed pilot tips and can be provided as either hand or rotary files.

The pilot tips on this family of instruments are distinguished by their fully-radiussed geometry which absolutely prevents the ledging of canals and their use-specific designs which allow unique functionality. While all of the instruments in this set of tools have pilot tips, alpha parabolas, and beta tapers, each of the three sets of instruments has a different function and therefore requires a different concept and sizing of pilot tips. In the access burs, the pilot tips vary by increments relating to coronal canal diameters in small, medium, and large roots; 0.2, 0.3, and 0.4 mm. These pilot tips become proportionally longer as the diameter increases between sizes. This helps prevent dangerous over-extension into curved canals.

In the initial enlargement files, the pilot tips are all 0.2 mm in diameter by 1 mm in length because they are designed to track the guidepath cut by the #15 negotiating file taken to length as prerequisite to rotary shaping. Because of the tracking function of these pilot tips, aggressive cutting flutes and relatively high speeds can be used in these files without forsaking safety.

In the finishing files, the pilot tips are again different as they are designed to self-gauge terminal canal diameters to tell dentists when the final shaping objective has been achieved. The shape is finished when the pilot tip of the finishing file matches the terminal diameter of the canal being shaped. The dentist finds out that the shape is finished when the next larger finishing file in the series refuses to move to full length in the canal because its larger pilot tip binds the terminus of the canal.

The parabolic flute shapes come immediately off of the cylindrical shank-end of the pilot tip and end a set distance back (typically 3-5 mm) between files in each of the series. The parabolic shape could be roughly described as a 0.10 taper with a radiussed bulge between points such that the shank end of the alpha region is tangential to the immediately adjacent beta profile. This is the parabolic alpha region of cutting flutes, and is expressly designed to cut shapes that funnel files and filling materials into and through the canal, ultimately to its terminus.

Behind this parabolic alpha zone is the beta region. This includes a flute pattern of consistent length and taper between files in each common series. In the preferred embodiment these flute portions have a 0.05 taper on the access burs and finishing files to impart a subtle taper to access line angles and coronal canal shapes. The initial enlargement files are different as their beta regions are parallel in shape and the flutes are dulled. This allows just their sharp alpha regions to cut safely around curvatures while the non-cutting beta region passively follows and augers out cut debris.

In the preferred embodiment, the access burs are made in rigid stainless steel or carbon steel. There is an alternate design which has diamond grit plated onto their alpha and beta regions. In the preferred embodiment, the initial enlargement files and the finishing files are made of nickel titanium alloy. All of these instruments, of whatever material, may be treated with hardening agents such as, but not limited to, titanium nitrite.

The access burs are intended to cut apically with their parabolic tip flutes when they are pushed into a canal orifice, as their pilot tips track the canal. The side-cutting flute design comes to play then as the bur is tipped up to the access line angle, cutting a straight-line entry path for all instruments and materials to follow. These burs are used at speeds of 5,000-20,000 RPM.

The initial enlargement files are preferably made of nickel titanium alloy and are used at 1200-1500 RPM to quickly cut a coronal shape in root canals. Each of the three files in this series has the same pilot tips with 0.2 mm diameters so they track the previously negotiated canal with their sharp parabolic tip flutes and they all have tapered non-cutting beta flutes to prevent the instruments from cutting into the inside of coronal canal curvatures.

The finishing series of parabolic files are also made of nickel titanium alloy but are used at slower speeds, approximately 300 RPM, as they are taken to the end of the canal being prepared. These instruments have pilot tips of varying sizes, sharp parabolic alpha flutes and sharp beta flutes with a 0.05 mm/mm taper, just enough canal shape to allow ease of entry and narrow enough to be safe in the smallest, most curved roots. These finishing files cut the larger apical preparations desired by many clinicians, an apical stop preparation albeit with a safe apical radius rather than the problematic ledgeform of traditional stop preparations.

The series of finishing files ratchet up in tip diameter in different intervals, small increments in between the smaller sizes of files used in challenging narrow canals and bigger jumps in tip diameter in the larger sizes of files, thus addressing a very wide range of apical canal diameters in as few as eight sizes total.

BRIEF DESCRIPTION OF THE DRAWINGS

A better understanding of the present invention may be realized from a consideration of the following detailed description, taken in conjunction with the accompanying drawings, in which:

FIGS. 7A-7D are schematic views of a first group of parabolic files in accordance with the present invention;

FIGS. 8A-8D are schematic views of another group of multi-taper files;

FIGS. 9A-9D are schematic views of still another group of multi-taper files;

FIGS. 10A-10D are schematic views of yet another group of multi-taper files;

FIG. 11 is an enlarged view, represented schematically, of one particular file of my parabolic file system;

FIG. 12 is a diagrammatic representation of a tip portion of the file of FIG. 11;

DESCRIPTION OF THE PREFERRED EMBODIMENTS

Figure 1:
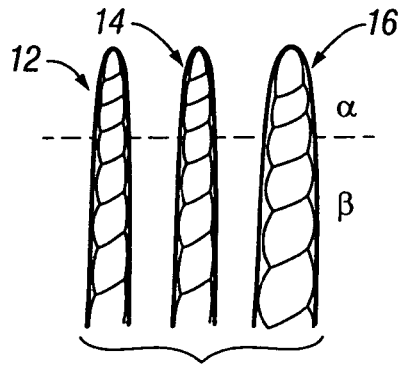
FIG. 1 shows a plurality of three parabolic files divided into alpha and beta sections.

FIG. 1 shows three tapered dental files 12, 14 and 16, in different sizes and each being divided into α and β sections. These represent multi-taper files of my prior application Ser. No. PCT/US02/03516. The files disclosed in that application include two distinct taper angles in the α and β sections with a definite change in angle occurring at the α-β juncture point.

Figure 2:
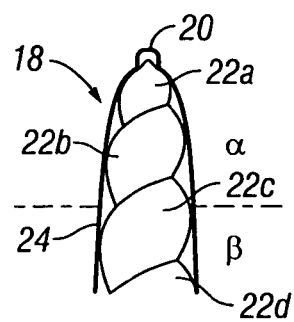
FIG. 2 is a view of one particular file in accordance with the invention and shows a pilot tip at the end of the alpha portion.
Figure 3:
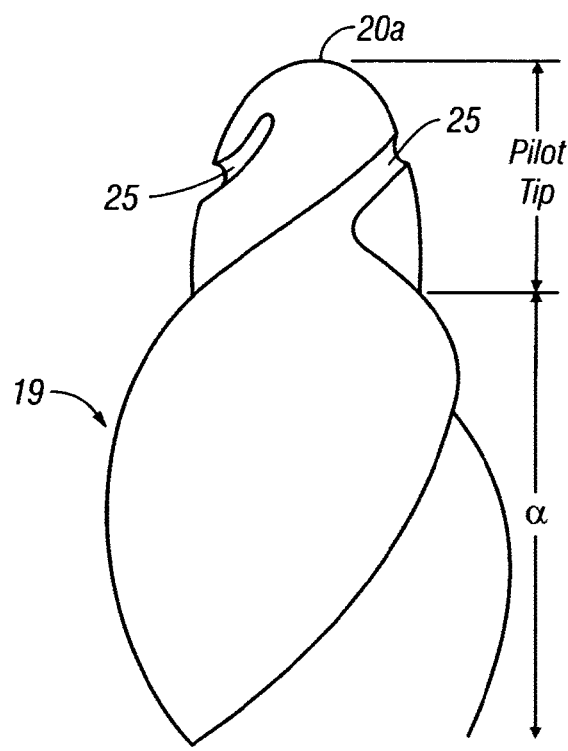
FIG. 3 is an enlarged view of the alpha portion and pilot tip of a file like FIG. 2 showing a modification thereof.

FIGS. 2 and 3 schematically represent different embodiments of the present invention. FIG. 2 depicts one particular file 18 having a pilot tip 20 and cutting flutes 22a-22d. The changes of taper angle from one cutting flute to the next are continuous in the form of a parabolic curve, indicated by the outline 24. The α and β portions of the file have different taper angles, and the change of taper from the α portion to the β portion is continuous over a radiussed curve shape.

FIG. 3 shows an enlargement of the pilot tip and a portions of a file 19, similar to that of FIG. 2. The pilot tip 20a is fully radiussed through 180 degrees, presenting a smooth surface at the forward end of the file which develops a guide path for the file and permits entry of the file into the root canal while avoiding ledging in the canal. The pilot tip 20a of the file 19 is provided with a spiral flute space 25 which serves to capture debris near the cutting edge of the file and remove it from the cutting tip. This spiral flute 25 has a non-cutting geometry.

Figure 4:
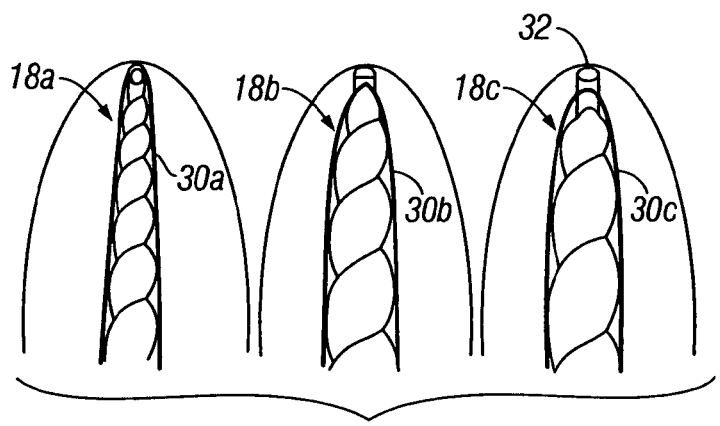
FIG. 4 shows files like those of FIG. 1 but with pilot tips provided in shapes corresponding to the parabolic outlines that extend outwardly, away from the terminus of the tips.

FIG. 4 depicts three parabolic curved files such as 18a, 18b and 18c. These are shown in position within corresponding root canals, indicated by the curved lines 30. These views represent a small diameter file 18a creating a pilot opening in the root canal.

FIG. 4 illustrates finishing files 18a, 18b and 18c of different sizes inserted into root canals 30a-30c. A smaller size file 18a makes the initial cut into the root canal. File 18b is of a larger size chosen to finish the root canal to its apical depth. File 18c is shown following the guide path cut by the file 18b but, because it is somewhat larger in diameter, it binds in the canal before reaching the terminal shape 32 which was cut by the pilot tip of the file 18b.

Figure 5A:
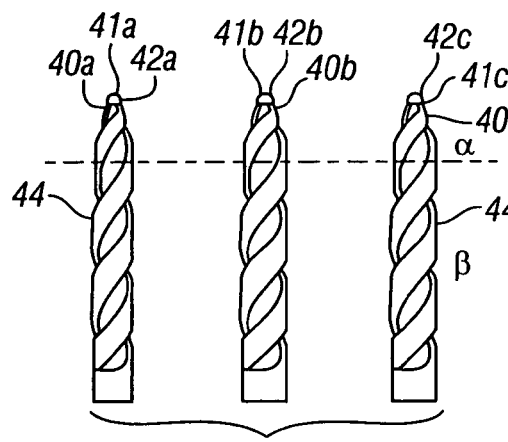
FIG. 5A is a view of three different burs in sizes small, medium and large with alpha and beta portions and pilot tips extending from the alpha portion.

FIG. 5A depicts a set of three access burs of different sizes, each having an α portion and a β portion, and designated small, medium and large. These access burs range from 40a in a small size through 40b, medium, and 40c, large. The access burs 40 are shaped to cut apically with the parabolic tip flutes 42a, 42b and 42c when inserted into a canal orifice, as the pilot tips 41a, 41b and 41c track the root canal. Side-cutting flutes 44 are of a fixed taper angle in order to cut a straight-line entry path for all instruments and materials to follow.

Figure 5B:
FIG. 5B is a schematic view showing a cross-section of a file of FIG. 5A.

FIG. 5B is an enlarged cross-sectional view of the access burs as shown in FIG. 5A.

Figure 6A:
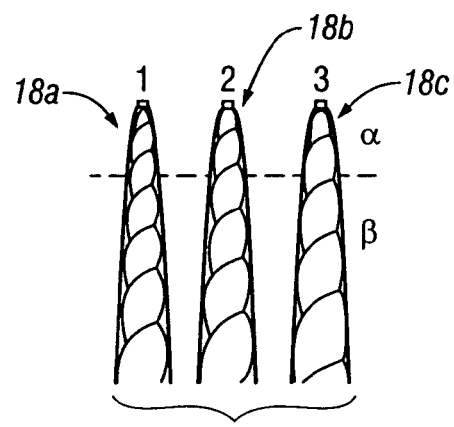
FIG. 6A is a view like that of FIG. 1, but with pilot tips extending from the depicted alpha portions.

FIG. 6A shows the α and β portions of the parabolic files 18a, 18b and 18c of FIG. 4.

Figure 6B:
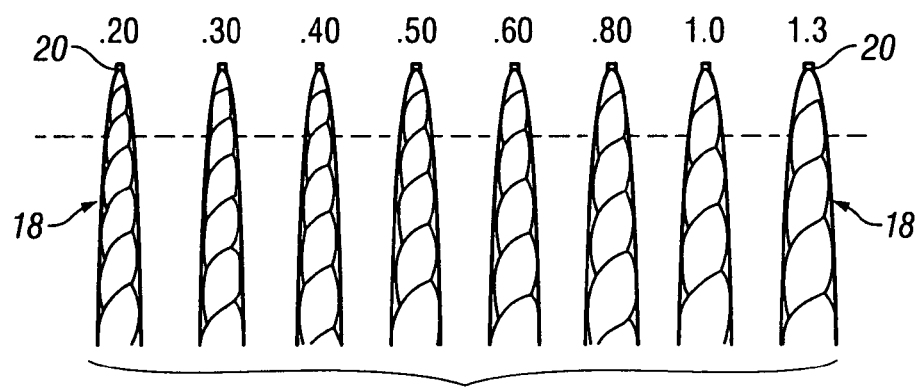
FIG. 6B shows a set of eight files with dimensions corresponding to what is set out in Table I above.

FIG. 6B shows a series of eight finishing files 18, all of different sizes and being parabolic in shape. In these files, the pilot tips 20 are of various sizes, corresponding to the size of the file 18. The size of these files of FIG. 6B range from 0.20 to 1.30 mm in diameter.

FIGS. 7A-7D schematically represent sets of four multi-tapered files 71, 72, 73 and 74 in accordance with the present invention. Each of the files is shown with a first portion α adjacent the tip 80 and a second portion β remote from the tip, extending back to the shank, not shown. The portions α and β have different tapers in the same file and the taper in the first portion also varies from file to file. In file 71 the taper of the first portion is 0.12. In file 72, the taper of the first portion is 0.10. In file 73, the taper of the first portion is 0.08. In file 74, the taper of the first portion is 0.06. In a first set of files represented by FIGS. 7A-7D, the taper of the second portion β is 0.02 mm/mm. In a second set of files, also represented by the drawings of FIGS. 7A-7D, the taper of the second portion β is 0.04 mm/mm. The files of FIGS. 7A-7D are discussed hereinabove. These and the remaining files of FIGS. 8-10 are provided with a radiussed surface in which the change of taper occurs gradually with distance from the tip from the taper of the first portion to the taper of the second portion. This is shown by the curve in the region C of FIGS. 7-10.

FIGS. 8A-8D schematically represent still another pair of sets of files in accordance with the invention. FIGS. 8A-8D show files 81, 82, 83 and 84 in a multi-tapered configuration. In each of the files 81-84, there is a first portion a adjacent the tip 90 and a second portion β remote from the tip, extending to the shank. In these sets of files, each of the first portions is a different length from those of the other first portions, being shortest for the file 81 which has the greatest taper of the first portion α (0.12) and increasing successively for files 82, 83 and 84 as the taper of the first portion diminishes, beginning at 0.10 for file 82 and ending with 0.06 for file 84.

As with the sets of files of FIGS. 7A-7D, one set of files 81-84 has a taper of 0.02 mm/mm for the second portion β whereas another set has a taper of 0.04 mm/mm for the second portion β.

FIGS. 9A-9D schematically represent another set of four multi-tapered files 91, 92, 93 and 94 in accordance with the present invention. Each of the files is shown with a first portion α adjacent the tip 100 and a second portion β remote from the tip, extending back to the shank, not shown. The portions α and β have different tapers in the same file and the taper in the first portion also varies from file to file. In file 91 the taper of the first portion is 0.12. In file 92, the taper of the first portion is 0.10. In file 93, the taper of the first portion is 0.08. In file 94, the taper of the first portion is 0.06.

In these files 91-94, the taper of the second portion varies from file to file, increasing in taper as the taper of the first portion reduces. For the file 91, the taper of the second portion is 0.01 mm/mm; for the file 92, it is 0.02; for the file 93 it is 0.03; and for the file 94 the taper of the second portion is 0.04 mm/mm.

FIGS. 10A-10D schematically represent still another set of files in accordance with the invention. FIGS. 10A-10D show files 101, 102, 103 and 104 in a multi-tapered configuration. In each of the files 101-104, there is a first portion α adjacent the tip 100 and a second portion α remote from the tip, extending to the shank. In this set of files, each of the first portions is a different length from those of the other first portions, being shortest for the file 101 which has the greatest taper of the first portion a (0.12) and increasing successively for files 102, 103 and 104 as the taper of the first portion diminishes, beginning at 0.12 for file 102 and ending with 0.06 for file 104.

In these files 101-104, the taper of the second portion varies from file to file, increasing in taper as the taper of the first portion reduces. For the file 101, the taper of the second portion is 0.01 mm/mm; for the file 102, it is 0.02; for the file 103 it is 0.03; and for the file 104 the taper of the second portion is 0.04 mm/mm.

The file depicted in enlarged form in FIG. 11 has diameters D1, D4, and D16, as well as the indicated length dimensions, corresponding to what is set forth in Table I. FIG. 12 represents various parabolic curves a, b, and c for the pilot tips of different files embodying the invention.

Figure 13:
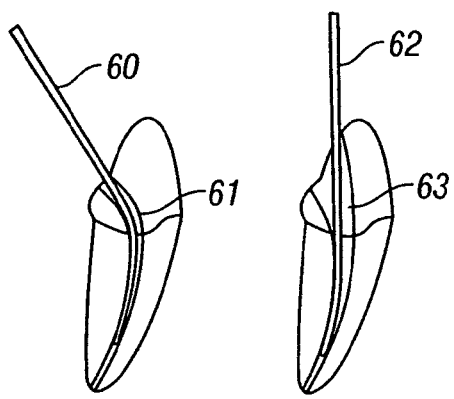
FIG. 13 shows two schematic views of a file in a curved root canal with the file bending to follow the contour of the canal.

FIG. 13 shows a pair of files 60 and 62 inserted in root canals of different shapes in two different teeth. File 60 is shown inserted into a root canal 61. File 62 is inserted into a root canal 63. The root canal 61 is more curved than the root canal 63 with the related file 60 assuming a corresponding shape in root canal 61 whereas the file 62 is relatively straight and the root canal 63 is more open at its proximal end than is the root canal 61.

Figure 14:
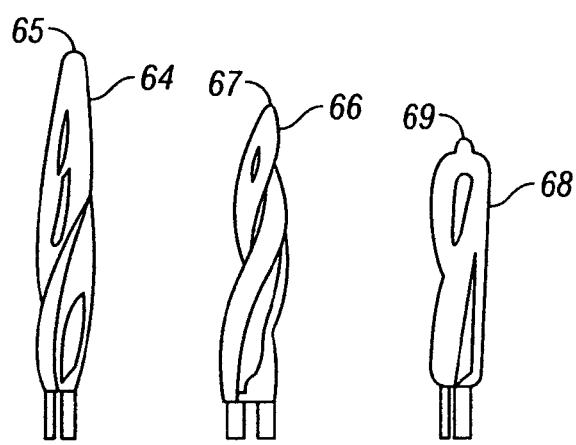
FIG. 14 depicts schematically three burs representing particular features of the invention.

FIG. 14 depicts a set of access burs 64, 66 and 68 of different shapes and sizes. However, each is provided with a pilot tip: 65 for bur 64; 67 for bur 66: and 69 for bur 68. Access burs 64 and 66 each have a parabolic shape extending rearward from the pilot tip.

Although there have been described hereinabove various specific arrangements of a ENDODONTIC INSTRUMENTS WITH PILOT TIPS AND PARABOLIC CUTTING FLUTES in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. An access bur for use in cutting a tapered access port into a root canal system of a tooth in apical and lateral directions, said bur comprising:
    a round shank having a first diameter;
    a non-cutting pilot tip at an end of the bur remote from said shank, said pilot tip having a second diameter which is smaller than said first diameter; and
    a tapered tip portion extending between said pilot tip and said shank comprising a first section (α) adjacent the pilot tip and a second section (β) adjacent the shank, each of the first section and the second section having a defined length and a cutting surface, said pilot tip having an end remote from the first section, said tapered tip portion having at least one material cutting portion comprising flutes and/or an abrasive surface throughout the defined lengths of the tapered tip portion, said tapered tip portion sized to provide said tapered access port into said root canal system;
    wherein said first section of said tapered portion has a continuously varying taper from said pilot tip adjacent said first section to said second section adjacent the shank;
    wherein the pilot tip extends forwardly from the first section for entering an upper opening in the root canal system as the bur shapes the opening by cutting the tapered access port into the canal system in the tooth; and
    wherein the bur is rigid, and is shaped, sized, and made of a material such that the bur is configured to rotate between 5,000-20,000 revolutions per minute to cut through the tooth and form the tapered access port.

2. The access bur of claim 1 wherein the cutting flutes of the second section are of a fixed taper angle in order to cut a straight-line entry path into the canal behind the pilot tip.

3. The access bur of claim 1 wherein the bur is fabricated of stainless steel.

4. The access bur of claim 1 wherein the bur is fabricated of carbon steel.

5. The access bur of claim 1 wherein said pilot tip presents a smooth surface to facilitate entry into a root canal without ledging therein.

6. The access bur of claim 5 wherein said pilot tip is hemispherical.

7. The access bur of claim 2 wherein the continuously varying taper of the first section has a parabolic cross-section.

8. The access bur of claim 1 wherein said material cutting portion has at least one spiral cutting edge.

9. The access bur of claim 1 wherein said material cutting portion has at least one abrasive surface comprising diamond grit.

10. A set of access burs for use in preparing a tapered access port into a root canal system comprising a plurality of access burs, each bur in said set of burs having differing profiles or dimensions and defined lengths from other burs in the set, comprising:
- a round shank having a first diameter;
- a pilot tip at an end of the bur remote from said shank, said pilot tip having a second diameter which is smaller than said first diameter; and
- a tapered tip portion extending between said pilot tip and said shank comprising a first section (α) adjacent the pilot tip and a second section (β) adjacent the shank, said tapered portion having at least one material cutting portion comprising flutes and/or an abrasive surface throughout the defined lengths of the tapered tip portion;
- wherein said first section (α) of said tapered portion has a continuously varying taper from said pilot tip adjacent the first section to said second section adjacent the shank;
- wherein the pilot tip of the bur extends forwardly from the first section, said first section shaping the tapered access port into the root canal system; and
- wherein the bur is rigid, and is shaped, sized, and made of a material such that the bur is configured to rotate between 5,000-20,000 revolutions per minute to cut through the tooth and form the tapered access port.

11. The set of access burs of claim 10 wherein the number of burs in said set is three.

12. The set of access burs in accordance with claim 10 wherein each bur in said set has a taper profile of its first section different from the taper profile of the first section of the other burs in said set.

13. The access bur of claim 1, wherein the pilot tip is fully radiused.

14. The set of access burs in accordance with claim 10, wherein the first section is configured to shape the tapered access port into the root canal system without ledging of the tapered accessport.

15. The access bur of claim 1, wherein the pilot tip has a diameter of between 0.2-0.4 mm.

* * * * *